(12) United States Patent
Juan et al.

(10) Patent No.: US 11,076,849 B2
(45) Date of Patent: Aug. 3, 2021

(54) SUTURE DELIVERY WITH ASYNCHRONOUS NEEDLE CAPTURE

(71) Applicant: TERUMO MEDICAL CORPORATION, Somerset, NJ (US)

(72) Inventors: Chun-Chia Juan, Taipei (TW); Yu-Shih Weng, Taipei (TW)

(73) Assignee: TERUMO MEDICAL CORPORATION, Somerset, NJ (US)

( * ) Notice: Subject to any disclaimer, the term of this patent is extended or adjusted under 35 U.S.C. 154(b) by 169 days.

(21) Appl. No.: 16/263,569

(22) Filed: Jan. 31, 2019

(65) Prior Publication Data
US 2019/0159774 A1 May 30, 2019

Related U.S. Application Data

(63) Continuation-in-part of application No. 14/726,963, filed on Jun. 1, 2015, now Pat. No. 10,194,901.
(Continued)

(51) Int. Cl.
*A61B 17/062* (2006.01)
*A61B 17/04* (2006.01)
*A61B 17/00* (2006.01)

(52) U.S. Cl.
CPC ...... *A61B 17/0625* (2013.01); *A61B 17/0057* (2013.01); *A61B 17/0469* (2013.01);
(Continued)

(58) Field of Classification Search
CPC ............ A61B 17/0625; A61B 17/0057; A61B 17/0469; A61B 17/0482; A61B 17/062;
(Continued)

(56) References Cited

U.S. PATENT DOCUMENTS

| 5,320,632 A | 6/1994 | Heidmueller |
| 5,417,699 A * | 5/1995 | Klein ................. A61B 17/0625 606/144 |

(Continued)

FOREIGN PATENT DOCUMENTS

| EP | 0647430 | 4/1995 |
| EP | 1674040 A2 | 6/2006 |

(Continued)

OTHER PUBLICATIONS

European Search Report and Written Opinion for co-pending European Application No. 17178418.4, dated Oct. 20, 2017.
(Continued)

*Primary Examiner* — Melanie R Tyson
*Assistant Examiner* — Uyen N Vo
(74) *Attorney, Agent, or Firm* — Dergosits & Noah LLP; Todd A. Noah

(57) ABSTRACT

An elongated deployment shaft carrying a needle deployment assembly with needles carrying sutures and a stabilizer. A catcher tube over the shaft having a catcher assembly at a distal end may retain a portion of the needles when passed through the tissue into engagement with catcher assembly. The catcher and needle deployment assemblies are configured to asynchronously engage the plurality of needles when moved distally beyond the catcher assembly. A sheath over the catcher tube may sandwich the tissue against the stabilizer when expanded. A first actuator may move catcher tube distally to decrease distance between proximal and distal ends of the stabilizer expand it and may move the sheath distally to sandwich the tissue. A second actuator may deflect the needles outward to move proximally through the tissue and engage the catcher and return a portion of each not retained by the catcher to a distal position.

18 Claims, 8 Drawing Sheets

Related U.S. Application Data

(60) Provisional application No. 62/729,312, filed on Sep. 10, 2018.

(52) U.S. Cl.
CPC ............. *A61B 2017/00663* (2013.01); *A61B 2017/00672* (2013.01); *A61B 2017/047* (2013.01); *A61B 2017/0472* (2013.01)

(58) Field of Classification Search
CPC .... A61B 2017/00663; A61B 2017/047; A61B 2017/0472
See application file for complete search history.

(56) References Cited

U.S. PATENT DOCUMENTS

| | | | |
|---|---|---|---|
| 5,458,609 A * | 10/1995 | Gordon | A61B 17/0469 606/144 |
| 5,964,773 A | 10/1999 | Greenstein | |
| 6,024,747 A | 2/2000 | Kontos | |
| 6,036,699 A | 3/2000 | Andreas et al. | |
| 6,280,460 B1 | 8/2001 | Bolduc et al. | |
| 6,355,050 B1 | 3/2002 | Andreas et al. | |
| 6,464,707 B1 | 10/2002 | Bjerken | |
| 6,896,685 B1 | 5/2005 | Davenport | |
| 7,879,049 B2 | 2/2011 | Dillon | |
| 9,668,724 B2 * | 6/2017 | Tang | A61B 17/0469 |
| 10,194,901 B2 * | 2/2019 | Tang | A61B 17/0057 |
| 10,201,345 B2 * | 2/2019 | Weng | A61B 17/0469 |
| 2002/0072768 A1 * | 6/2002 | Ginn | A61B 34/76 606/213 |
| 2005/0216037 A1 | 9/2005 | Davenport | |
| 2010/0016810 A1 | 1/2010 | Drews | |
| 2010/0145364 A1 | 6/2010 | Keren et al. | |
| 2011/0288563 A1 | 11/2011 | Gianotti | |
| 2012/0296347 A1 * | 11/2012 | Roorda | A61B 17/0469 606/145 |
| 2012/0296373 A1 | 11/2012 | Roorda et al. | |
| 2013/0165956 A1 | 6/2013 | Sherts et al. | |
| 2013/0178872 A1 | 7/2013 | Shriver | |
| 2014/0249552 A1 | 9/2014 | Tang et al. | |
| 2015/0257753 A1 | 9/2015 | Tang et al. | |

FOREIGN PATENT DOCUMENTS

| | | |
|---|---|---|
| JP | 2001522269 | 11/2001 |
| JP | 2002502658 | 1/2002 |
| JP | 2002537887 | 11/2002 |
| JP | 2003509175 | 3/2003 |
| JP | 2003511187 | 3/2003 |
| WO | 05/112789 | 12/2005 |
| WO | 07/025302 | 11/2007 |
| WO | 11/112721 | 9/2011 |

OTHER PUBLICATIONS

European Search Report from corresponding European Patent Application 17163400.9, dated May 23, 2017, pp. 1-8.
International Preliminary Report on Patentability for International Application No. PCT/IB2015/001590; dated Dec. 6, 2016.
International Search Report and Written Opinion for International Application No. PCT/IB2015/001590; dated Jan. 21, 2016.
International Search Report dated May 14, 2014 in corresponding PCT Application No. PCT/US2014/017813.
Notification of Reason for Refusal, issued for Korea Patent Application No. 10-2016-7036490, dated Jan. 16, 2018.
Notification of Reasons for Refusal issued in Japan Application No. 2015559021, dated Sep. 5, 2017.
Office Action for U.S. Appl. No. 14/726,963, dated Feb. 9, 2018.
Office Action for U.S. Appl. No. 14/726,996, dated Feb. 6, 2018.
Search Report and Written Opinion International Patent Application No. PCT/US2020/016103, dated May 25, 2020.

* cited by examiner

SUTURE DELIVERY WITH ASYNCHRONOUS NEEDLE CAPTURE

RELATED APPLICATIONS

This application claims priority to and the benefit of U.S. Provisional Patent Application Ser. No. 62/729,312, filed Sep. 10, 2018 and is a continuation-in-part application of U.S. application Ser. No. 14/726,963, filed Jun. 1, 2015, now U.S. Pat. No. 10,194,901, which is claims priority to and the benefit of U.S. Provisional Patent Application Ser. No. 62/006,709 filed Jun. 2, 2014, and is a continuation-in-part application of U.S. application Ser. No. 14/186,246, filed Feb. 14, 2014, each of which is incorporated herein in its entirety by reference.

FIELD OF THE PRESENT DISCLOSURE

The present disclosure relates generally to techniques and devices for closing openings in a patient's vasculature or other body lumens. For example, the present disclosure relates to systems, devices, and methods for suturing of arterial and venous puncture sites to approximate tissue around the opening, such as may be required following a surgical procedure.

BACKGROUND

To improve recovery time, a variety of interventional and diagnostic procedures may be carried out in a minimally invasive manner by accessing a desired location within a patient's body. By introducing catheters or other elongated devices into the vasculature at a convenient entry point, such procedures may be performed at a remote location by guiding the device through the body lumen to the desired position. Although these techniques represent less impact on the patient than conventional open procedures, access to the vasculature requires forming an opening in an artery or vein that subsequently must be repaired.

A variety of methods may be used to close the access opening. Conventionally, hemostasis may be achieved through manual compression to substantially reduce the flow of blood through the opening and allow clot formation. Although generally successful, compression may take a significant amount of time and may be associated with considerable patient discomfort. Additionally, complications such as unintended total occlusion of the lumen that may result in ischemia or thrombosis can occur. These aspects may be exacerbated depending upon the size of the opening necessary to introduce the device, whether anticoagulants are employed and on the condition of the patient.

To ameliorate these problems, techniques for suturing the opening to achieve hemostasis and reduce time to ambulation have been developed. In order to maintain the minimal invasiveness of the procedure, many of these techniques are adapted to be performed. For example, the suture delivering device may be introduced through the same opening used to perform the procedure. Typically, one or more needles are deployed by the suture delivering device to pierce the vessel wall and draw the suture material through so that the suture may be secured over the adventitial surface and close the opening.

Despite the benefits associated with the use of suture delivering devices, a number of challenges exist. In particular, it is desirable for the needle or needles to be positioned accurately with respect to the vessel wall so as to pierce the tissue far enough away from the opening to result in a sufficiently robust location for the suture. It is also desirable to provide a device configured to deploy and actuate the needles in a reproducible manner to minimize the amount of skill required from the operator. In U.S. application Ser. No. 14/726,963, incorporated by reference as noted above, embodiments are disclosed in which multiple needles carrying suture material are captured by the suture delivering device after being passed through tissue. Although the disclosed embodiments address these challenges as described in that application, an actuation force is associated with engaging and thereby capturing the needles. As will be appreciated, this actuation force is approximately a multiple of the number of needles being captured, with each component of the actuation force corresponding to the amount of force needed to engage one of the needles. Accordingly, this disclosure is directed to systems and methods for suturing an opening in a body lumen that retain the desired advantages, including reproducibly deploying needles to suture tissue, while also reducing the necessary actuation force.

SUMMARY

This disclosure includes a suture delivery device for suturing tissue. The suture delivery device may include an elongated deployment shaft, a needle deployment assembly carried by the shaft, including a plurality of needles carrying suture material configured to have an insertion profile at a distal position and to deflect radially outwards to a piercing angle when moved proximally relative to the shaft, a stabilizer carried by the shaft at a location proximal of the needle deployment assembly, wherein the stabilizer is reconfigurable between an unexpanded insertion profile and an expanded profile, a catcher tube coaxially and slidably disposed over the shaft having a catcher assembly at a distal end, wherein the catcher assembly and needle deployment assembly are configured to asynchronously engage and retain at least a portion of each of the plurality of needles carrying the suture material when the needles are passed through the tissue to be sutured to a proximal position beyond the catcher assembly and then returned distally, and a sheath coaxially and slidably disposed over the catcher tube, wherein a distal end of the sheath is configured to sandwich tissue to be sutured against the stabilizer when expanded.

In one aspect, distal movement of the needle deployment assembly may cause a first subset of the needles to engage the catcher assembly at a first time and continued distal movement of the needle deployment assembly may cause a second subset of the needles to engage the catcher assembly at a second time subsequent to the first time.

In one aspect, an actuation force associated with engaging the first subset of the needles and an actuation force associated with engaging the second subset of the needles may be each less than an actuation force required to engage all the needles simultaneously.

In one aspect, the catcher assembly may be configured to engage a detachable needle tip of each of the plurality of needles.

In one aspect, the capture assembly may have a plurality of capture points. The plurality of capture points may be longitudinally spaced with respect to each other. Each of the plurality of capture points may be created by a catching element. Each catching element may be configured to engage a different subset of the needles.

In one aspect, each catching element may have a disk configuration. Alternatively, each catching element may have a dished configuration. The catcher assembly may have nested dished catching elements.

In one aspect, a single catching element may define the plurality of capture points. The catching element may have a chair shaped configuration.

In one aspect, the plurality of needles may be a first subset of needles having a first length and a second subset of needles having a second length, such that the second length is shorter than the first length.

This disclosure also includes methods for delivering a suture. For example, a suitable method may include providing an elongated deployment shaft, a needle deployment assembly carried by the shaft, including a plurality of needles carrying suture material, a stabilizer carried by the shaft at a location proximal of the needle deployment assembly, a catcher tube coaxially and slidably disposed over the shaft having a catcher assembly at a distal end, and a sheath coaxially and slidably disposed over the catcher tube, advancing the elongated deployment shaft to a desired position in a patient, reconfiguring the stabilizer from an unexpanded insertion profile to an expanded profile, sandwiching tissue to be sutured between a distal end of the sheath and the expanded stabilizer, deflecting the plurality of needles radially outwards to a piercing angle from an insertion profile at a distal position with proximal movement relative to the shaft, moving the plurality of needles to a proximal position beyond the catcher assembly by passing through the tissue to be sutured, engaging the catcher assembly with a first subset of the plurality of needles at a first time when moved distally from the proximal position, engaging the catcher assembly with a second subset of the plurality of needles at a second time subsequent to the first time after further distal movement, retaining at least a portion of each of the plurality of needles carrying the suture material with the catcher assembly and returning a portion of each of the plurality of needles not retained by the catcher assembly to the insertion profile at the distal position.

In one aspect, an actuation force associated with engaging the first subset of the needles and an actuation force associated with engaging the second subset of the needles may be each less than an actuation force required to engage all the needles simultaneously.

In one aspect, the catcher assembly may have a plurality of capture points, such that the first subset of needles only engages a first capture point and the second subset only engages a second capture point.

In one aspect, the plurality of needles may be a first subset of needles having a first length and a second subset of needles having a second length, such that the second length is shorter than the first length. The catcher assembly may engage the first subset of needles at the first time and may engage the second subset of needles at the second time.

In one aspect, engaging the catcher assembly with the plurality of needles may allow a detachable needle tip of each needle to be retained.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
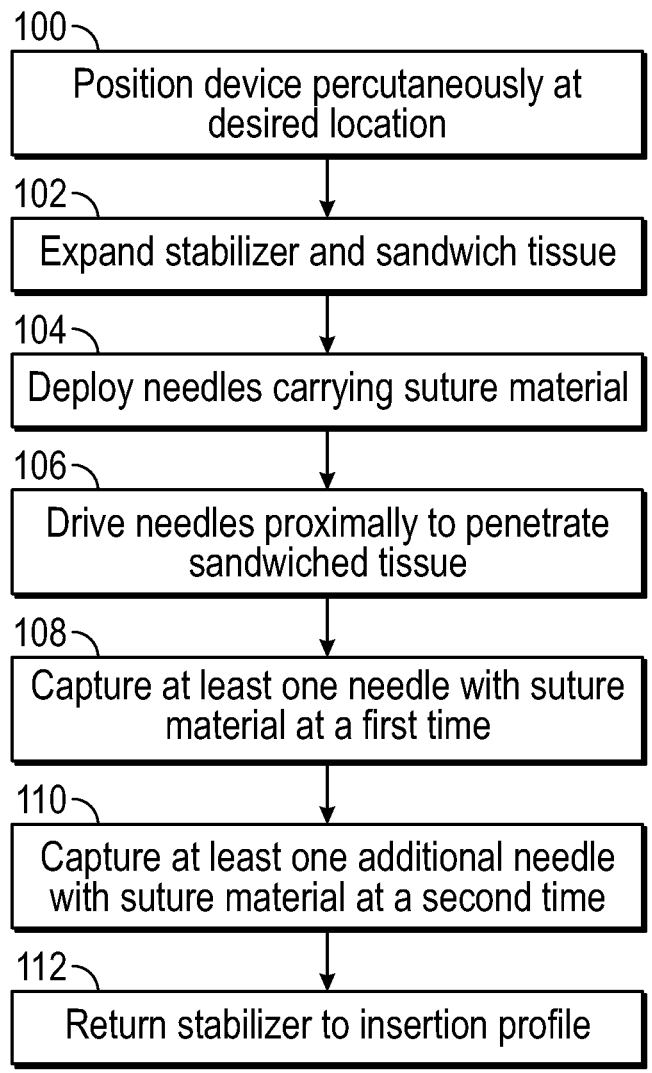
FIG. 1 depicts a flowchart representing a suitable routine for delivery sutures with asynchronous needle capture, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. For example, the term "suturing" includes drawing two surfaces or edges together with a flexible material to close a puncture, opening, or other wound, wherein the suture is a material that may be synthetic or natural, such as a polymer, gut, metallic wire or other suitable equivalents.

Finally, as used in this specification and the appended claims, the singular forms "a," "an" and "the" include plural referents unless the content clearly dictates otherwise.

According to this disclosure, a device for applying sutures to promote hemostasis following an interventional procedure may be configured to perform a sequence of operations associated with positioning the device in the patient's vasculature, sandwiching tissue using an expanded portion of the device to stabilize the tissue for suture deployment, deploying needles carrying suture material at a piercing angle to pass them through the stabilized tissue and returning the device to an unexpanded condition to release the sandwiched tissue and allow the device to be withdrawn. In particular, as will be described below, aspects of this disclosure details techniques for automating at least some of these operations using actuators that cause the device to perform the operations in a reproducible manner. For example, a first actuator may be employed to expand the a distal portion of the device and sandwich the tissue and a second actuator may be used to deploy needles carrying suture material at a piercing angle and drive them through the sandwiched tissue, to capture the penetrating ends of the needles and to return the distal portion of the device to its unexpanded condition. Further, the disclosed embodiments are also configured to reduce an actuation force associated with capturing the needles by asynchronously engaging the needles carrying suture material.

Turning now to FIG. 1, an example routine for deploying sutures using a device of this disclosure may therefor include generally begin with 100 to position the device at a desired location, such as by using a bleed back lumen with a port in the distal end of the device so that when the port is located within the vessel, blood will enter the port, flow through the lumen and provide a visual indication at the proximal portion of the device. Following positioning, in 102 soft tissue at the desired suture site is stabilized by expanding a stabilizer on a distal portion of the device and sandwiching the tissue between the stabilizer and a portion of the device that is relatively more proximal. The distal expandable stabilizer exhibits a reduced insertion profile and an expanded profile for stabilizing tissue during delivery of the sutures. Relative movement of the stabilizer may allow tissue to be secured between the stabilizer and the relatively more proximal portion and provide a target for needle-deployed sutures carried by the device. As will be appreciated from the discussions below, the relative movement may involve movement of the stabilizer towards the proximal portion, movement of the proximal portion towards the stabilizer, or both. The sandwiched tissue may include portions of the vessel wall surrounding the puncture being closed.

Next, in 104, a plurality of needles carrying suture material that are disposed distal of the sandwiched tissue are deployed at a piercing angle so that movement of the needles to a proximal position in 106 penetrates the sandwiched tissue. Following penetration of the sandwiched tissue by the needles, the plurality of needles are moved distally from the proximal position. A first subset of the needles, such as at least one of the needles, is captured proximally in 108 at a first time. In some embodiments, this may include capturing at least a portion of the needle, such as a detachable needle tip that carries the suture material as described below. At a second, subsequent time, a second subset of the needles, different than the first subset, is captured distally in 110. The asynchronous capture in the embodiments described below generally involves engaging and capturing all of the needles at either the first or second time, such as by capturing a subset comprising approximately half of the needles at the first time and capturing a subset comprising the remainder of the needles at the second time. However, it will be appreciated that other embodiments are possible within the scope of this disclosure, and any number of asynchronous capture times may be employed, and indeed, in some embodiments, each needle may be captured at its own discrete time. To prepare for withdrawal of the device, in 112 the stabilizer and needle deployment mechanism are returned to their delivery configuration. According to the techniques of this disclosure, it may be desirable to automate some or all of these operations. For example, in an embodiment, a first actuator may be used to perform 102 and a second actuator may be used to perform 104-112. Any suitable actuator configuration, including a push button, slide slider, pull lever and/or push plunger may be employed. Any desired number and sequence of operations may be coordinated and/or automated by linking the operations to a single actuator.

Figure 2:
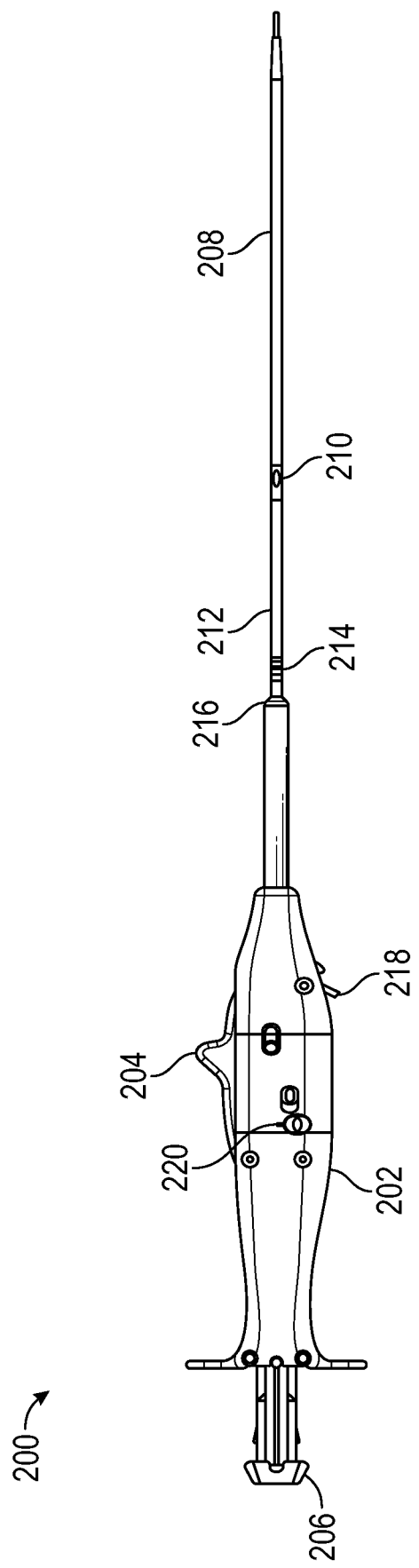
FIG. 2 schematically depicts an overview of a suture delivery device of FIG. 1, according to one embodiment.

To help illustrate aspects of this disclosure, FIG. 2 is a schematic overview of a suture delivering device 200 according to one embodiment. Device 200 includes handle 202 having a first actuator configured as slider 204 and a second actuator configured as plunger 206. The elongated distal portion of device 200 includes catheter 208 for deployment within a patient's vessel. Guidewire exchange port 210 may be used to facilitate advancement of catheter 208 over a guidewire already positioned within the patient's vasculature using known techniques. Proximal to catheter 208 is needle deployment assembly 212 and stabilizer 214. Stabilizer 214 may be reconfigured between the reduced profile shown for insertion and an expanded configuration. While in its expanded configuration, relative movement between the distal end of sheath 216 and stabilizer 214 may be used to sandwich tissue in preparation of suture delivery. In this embodiment, slider 204 may be actuated to expand stabilizer 214 and generate the relative movement between sheath 216 and stabilizer 214. Further, plunger 206 may be actuated so that the plurality of needles within needle deployment assembly 212 are first lifted from their insertion profile to a piercing angle and then driven to penetrate the tissue sandwiched between stabilizer 214 and sheath 216. Continued actuation of plunger 206 may cause at least a portion of the needles to be captured within sheath 216. Subsequently, stabilizer 214 and needle deployment assembly 212 are returned to their insertion profile to facilitate withdrawal of device 200. As shown, device 200 may include a bleed back indicator 218 on handle 202 which is in communication with a port positioned adjacent stabilizer 214 to provide visual feedback in the form of blood flow when stabilizer 214 is positioned within the patient's vessel. Additionally, device 200 may include release trigger 220 to return stabilizer 214 to its insertion profile without actuating plunger 206 and performing the associated operations if it becomes desirable to abort the procedure without deploying the needles and suture material.

In one embodiment, device 200 may include a catheter hemostasis valve proximal of guidewire exchange port 210. The valve may be positioned within catheter 208 and may include one or more flexible valves with an extending body to form a lumen between the valve and guidewire exchange port 210 to facilitate introduction of a guidewire with a ramp to ease the transition to the lumen. A stopper on the valve may help secure the valve within catheter 208, such as by using adhesives, crimping ring, friction or any other suitable methods. The flexible valve(s) may be configured to allow the guidewire to pass through and to block blood flow when the guidewire is withdrawn.

Figure 3:
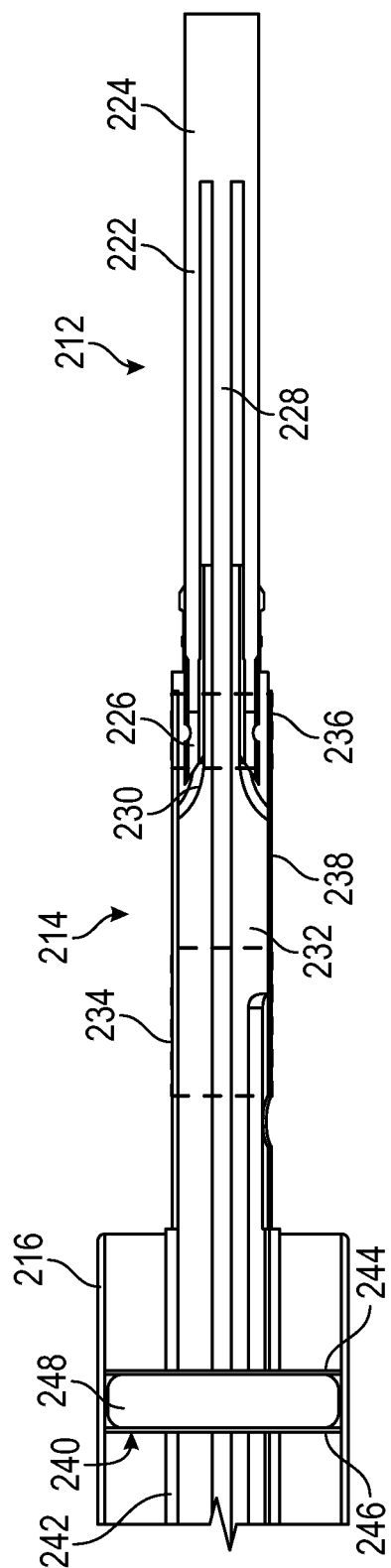
FIG. 3 schematically depicts a detail view of a needle deployment assembly, stabilizer and catcher assembly of a suture delivery device, according to one embodiment.

Further details regarding this embodiment are depicted in FIG. 3, which schematically shows needle deployment assembly 212 and stabilizer 214. Needle deployment assembly 212 includes a plurality of needle bases 222 projecting proximally from needle pushing element 224, which may be implemented as a piston or other suitable structure, with each needle having a detachable needle tip 226. Suture material may be threaded through or otherwise secured to an aperture in needle tip 226 (not shown in the figure for the sake of clarity). Trigger wire 228 is secured to piston 224 and extends proximally to handle 202 for actuation by plunger 206 as described in further detail below. For delivery, needle bases 222 and tips 226 are positioned distally of corresponding ramps 230 formed at the distal end of shaft 232. Trigger wire 228 is slidably disposed coaxially within shaft 232 so that relative proximal movement of trigger wire 228 causes needle bases 222 and tips 226 to be deflected radially outward to a piercing angle by ramps 230. Stabilizer 214 is formed by proximal band 234 and distal band 236 that are joined by at least one deflectable wing 238. Proximal band 234 is secured to catcher tube 242, which is coaxially disposed and slidable over shaft 232. Correspondingly, distal band 236 is secured to shaft 232. In turn, catcher assembly 240, secured to catcher tube 242, is coaxially disposed and slidable within sheath 216. By moving catcher tube 242 and catcher assembly 240 distally relative to shaft 232, the distance between proximal band 234 and distal band 236 may be decreased, causing deflectable wings 238 to project radially outwards to expand stabilizer 214 from its insertion profile.

In this embodiment, catcher assembly 240 includes two catching elements, a distal catcher disk 244 and a proximal catcher disk 246, separated by spacer 248. Once at least a portion of the plurality of needles, such as needle tips 226, have been passed proximally through the tissue to be sutured and are located at a proximal position relative to distal catcher disk 244 and proximal catcher disk 246, the plurality of needles may be returned in a distal direction so that at least a portion of each of the plurality of needles are asynchronously captured. As will be described in further detail below, proximal catcher disk 246 is configured so that it is engaged by only a subset of needle tips 226, while distal catcher disk 244 is configured to only engage the remaining subset of needle tips 226. Proximal catcher disk 246 creates a first capture point, so that the needle tips 226 that it engages are captured at a first time, and spacer 248 positions distal catcher disk 244 at a second capture point, so that the remaining needle tips 226 engage it at a second time. Thus, needle tips 226 are captured asynchronously, with an actuation force being required to engage the first subset of needle tips 226 at the first time and a similar actuation force required to engage the second subset of needle tips 226 at the second time. Capturing the multiple needle tips 226 by the catcher assembly 240 generates the disengagement force between the needle tips 226 and needle bases 222. The disengagement force is correlated to the actuation force applied by the user to needle pushing element 224. For purposes of comparison, the actuation force required at any one time in the present embodiment is approximately half that required for the embodiments disclosed in incorporated U.S. application Ser. No. 14/726,963 in which the needle tips are engaged simultaneously. As will be appreciated, further reductions in the needed actuation force at any one time could be achieved by using a catcher assembly having additional capture points so that fewer needles are being engaged at any given time.

Figure 4:
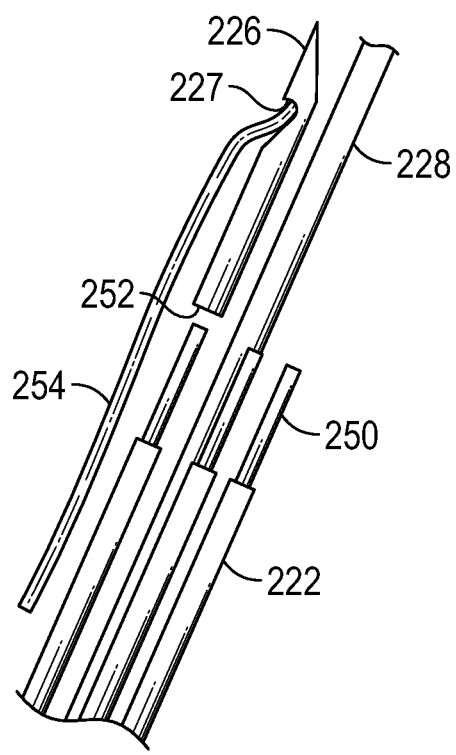
FIG. 4 schematically depicts a needle tips and needle bases, according to one embodiment.

Details regarding needle assembly 212 are shown in FIG. 4, which schematically depicts the interaction between needle bases 222 and needle tips 226. As shown, each needle base 222 may include post 250 configured to fit within recess 252 of needle tip 226. It may be desirable to position needle tips 226 at a specific rotational orientation with respect to needle bases 222. In one aspect, an asymmetric configuration of post 250 and corresponding recess 252 may secure needle tips 226 at the desired rotational orientation. For example, ribs or other similar features on post 250 may mate with complementary features of recess 252. Other means of securing needle tip 226 to needle base 222 may be employed as desired, such as using a post on the needle tip and a recess in the base. Suture material 252 may be retained in aperture 227 of needle tip 226 using any suitable method, such as crimping, heating, knotting or using adhesives or plug. As noted, needle tips 226 may be detachable from needle bases 222. A variety of techniques may be employed to achieve a desired degree of retention between needle tip 226 and base 222. For example, needle tip 226 may be crimped prior to or after placement on post 250 or some other form of structural interaction may be created. In other embodiments, adhesive may be used or recess 252 may be sized somewhat smaller than post 250 and needle tip 226 may have a split, allowing the elasticity of the tip material to retain it in position. The surface quality and coating of post 250 may also influence the retention of needle tip 226. For example, one or both of needle base 222 and needle tip 226 may be formed from a nickel-titanium alloy such as Nitinol having super elastic and shape memory characteristics or stainless steel. In one aspect, either or both of needle base 222 and needle tip 226 may have a layer of nitinol oxide to have a proper retention. Although embodiments are discussed in the context of four needles, any suitable number of needles may be employed as desired.

Figure 5:
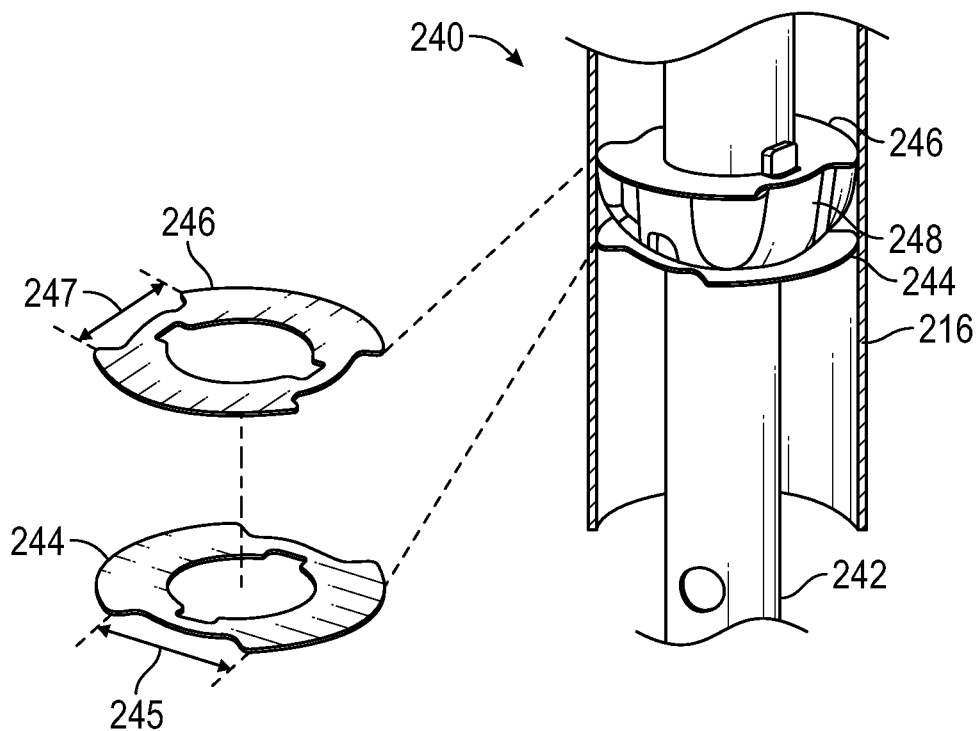
FIG. 5 schematically depicts a catcher assembly having disk catching elements, according to one embodiment.

Turning now to the schematic detail view of FIG. 5, it may be seen that distal catcher disk 244 and proximal catcher disk 246 of catcher assembly 240 may have configurations in which each disk selectively engages only one subset or the other of needle tips 226. For example, rather than exhibiting a completely circular profile, distal catcher disk 244 has opposing gaps 245 through which one or more needle tips 226 may pass without engaging distal catcher disk 244. The remainder of the perimeter of distal catcher disk 244 is sized to conform closely to the inner diameter of sheath 216, to that needle tips 226 are captured when moved distally after having been advanced proximally past the edge. Accordingly, distal catcher disk 244 engages one subset but not the other subset of needle tips 226. Proximal catcher disk 246 has a similar configuration with opposing gaps 247. By orienting distal catcher disk 244 and proximal catcher disk 246 so that gaps 245 and gaps 247 are rotated approximately 90° with respect to each other allows distal catcher disk 244 to engage one subset of the needle tips 226 and proximal catcher disk 246 to engage the other subset. The depicted embodiment is configured for use with four needle tips 226, each spaced at approximately 90° with respect to each other around needle assembly 212. It will be appreciated that in other embodiments having different numbers of needles, different numbers of catcher disks and/or gaps with different relative orientations may be employed so that only some needle tips are engaged by each of the different catcher disks in order to effect the asynchronous capture characteristic of this disclosure.

Figure 6:
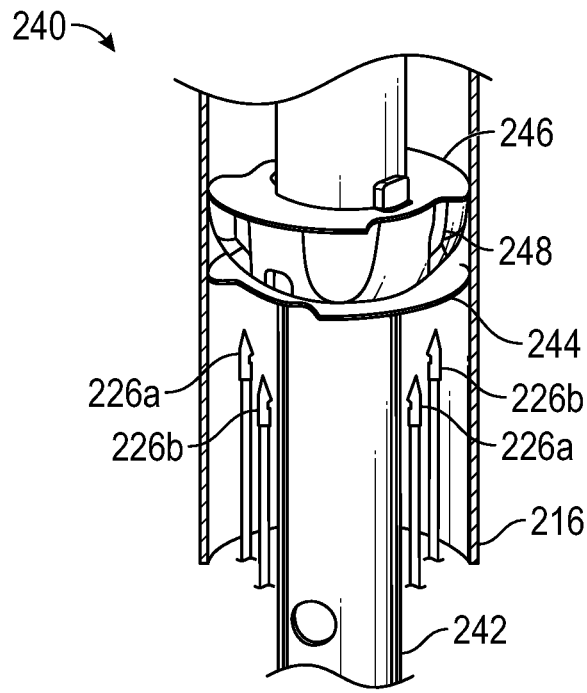
FIGS. 6-8 schematically depict asynchronous engagement of needle tips with the catcher assembly of FIG. 5.
Figure 7:
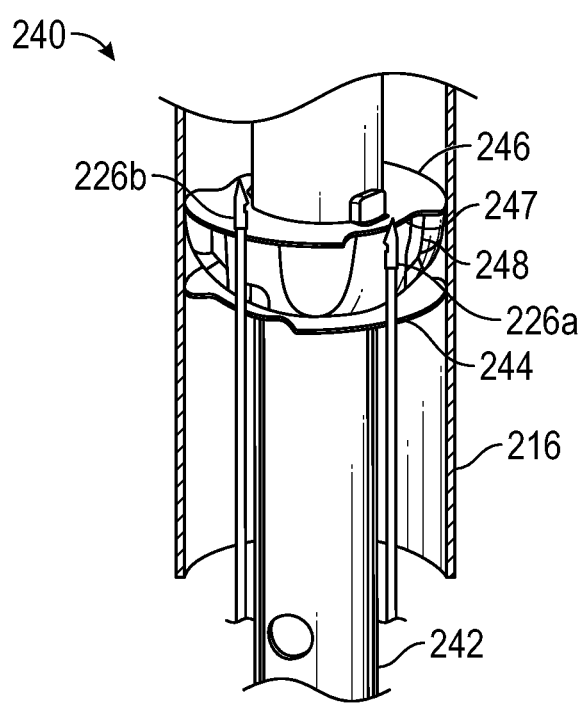

As noted, suture delivery with needle deployment assembly 212 may involve an outward radial deflection of the needles to a piercing angle configured to penetrate the sandwiched tissue from a distal to proximal direction, followed by the asynchronous capture of at least a portion of the needles, such as needle tips 226 carrying suture material 254. Details regarding aspects of these operations are schematically illustrated in the sequence of FIGS. 6 and 7. Prior to deployment, needle tips 226 and their associated needle bases 222 exhibit a reduced profile for insertion by conforming to shaft 232, such as by lying in recesses (such as shown in FIG. 3). Once needle tips 226 and needle bases 222 have been driven proximally by needle pushing element 224 and trigger wire 228 (as also described in reference to FIG. 3), needle tips 226 and needle bases 222 are deflected outwards by ramps 230 and enter a radial space between sheath 216 and catcher assembly 240 after passing through the tissue to be sutured.

Figure 8:
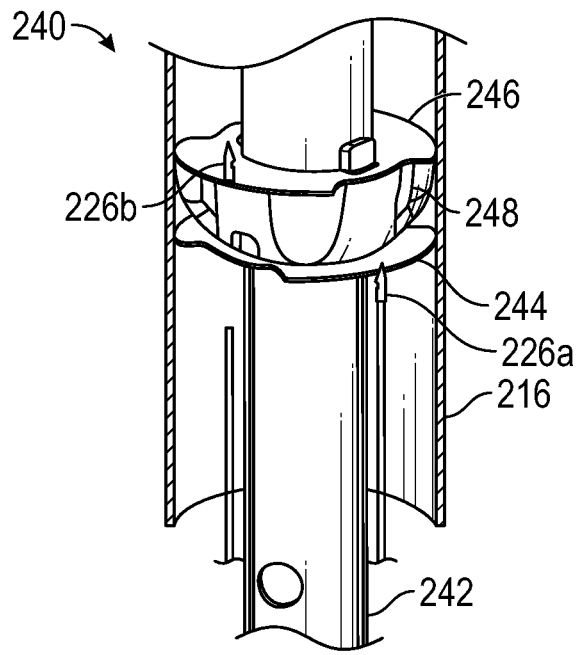

Beginning with FIG. 6, the four needles of this embodiment are shown, with a first subset of needle tips 226a and a second subset of needle tips 226b. At this stage, all the needle tips are positioned distally of catcher assembly 240. Next, FIG. 7 shows the configuration after needle tips 226 have been driven to a proximal position relative to catcher assembly 240. In this view, only one of each needle tip subset is shown for the sake of clarity. In particular, it may be seen that distal catcher disk 244 and proximal catcher disk 246 selectively engage and capture different subsets of the needle tips 226. For example, when the plurality of needles is returned in a distal direction from the proximal position beyond catcher assembly 240, needle tip 226a does not engage proximal catcher disk 246 because it is aligned with gap 247. Conversely, needle tip 226b, although able to travel substantially freely past distal catcher disk 244 due to the alignment with gap 245, is engaged and captured by the edge of proximal catcher disk 246 at this first capture point. Correspondingly, the actuation force need only be sufficient to engage the subset of needle tips 226b and dislodge them from their respective needle bases. Then, in FIG. 8, needle tip 226b has been captured by the edge of proximal catcher disk 246, and after further distal movement, needle tip 226a is engaged by the edge of distal catcher disk 244 after moving freely past proximal catcher disk 246 because of the alignment with gap 247 noted above (again, only one of each needle tip subset is shown for the sake of clarity.) Likewise, the actuation force at this subsequent time need only be sufficient to engage the subset of needle tips 226a. The longitudinal spacing of distal catcher disk 244 and proximal catcher disk 246 thereby causes the asynchronous capture of needle tips 226, with needle tips 226b captured at a first time and needle tips 226a captured at a subsequent second time. If desired, the distal portion of catcher assembly 240 may have a conically shaped configuration to help guide the needle tips appropriately. As the respective needle tips 226 are moved distally, the edges of the capture disks 244 and 246 and the inner surface of sheath 216 cooperate to retain the needle tips 226 so that distal movement of the needle bases disengages the tips from the bases and they remain captured along with their associated suture material (also not shown in this view for the sake of clarity.) Due to the relative placement of gaps 245 and 247, each capture disk 244 and 246 is configured to engage one subset or the other of the plurality of the needles.

Sheath 216 defines an outer boundary of needle travel path so that catcher assembly 240, coaxially disposed inside the sheath 216, defines the inner boundary. Sheath 216 along with distal catcher disk 244 and proximal catcher disk 246 of catcher assembly 240 may be sized and positioned relative to each other to either define a small radial space or to be in contact radially at one point or more, other than at the specific areas defined by gaps 245 and 247. Thus, needle tips 226 may pass longitudinally between sheath 216 and catcher assembly 240. In one embodiment, a small radial space may exist between the edges of catcher disks 244, 246 and sheath 216, being sized to allow needle passage until sufficient friction retains at least a portion of the needle(s) between catcher assembly 240 and sheath 216. Needle capture and retention may be created by friction against catcher disks 244, 246 and sheath 216 having sufficient force to disengage needle tip 226 from needle base 222 when needle deployment assembly 212 is retracted in the distal direction. Alternatively, proximal edges of catcher disks 244, 246 may be in contact with sheath 216 so that no space or a space smaller than the dimension of needle tip 226 exists (other than at gap 245 and 247), but one or both the materials are sufficiently compliant to deform and allow passage of needle tip 226. In one aspect, needle tip 226 may be wider in dimension than needle base 222, creating proximal edge 252 as shown in FIG. 4 to facilitate engagement. For example, the needle tip and needle base may be 0.5 mm and 0.4 mm in outer diameter respectively. As such, catcher disks 244 and 246 may engage the needle tips 226 at this proximal edge. Alternatively, needle tips 226 may employ any other suitable features configured to facilitate engagement and capture of the needle tips, such as a recess, notch or the like. In embodiments exhibiting a radial gap between sheath 216 and catcher assembly 240, the space may be substantially constant longitudinally along the device or may taper, so that it is wider near the distal end to facilitate entry of needle tip 226 and narrower towards the proximal end to provide increasing friction for retention of needle tip 226. The friction may be enhanced by selecting materials having the desired properties for catcher assembly 240 and/or sheath 216. Similarly, the friction may also be increased by the mechanical design. In other embodiments, significant friction between needle tip 226 and needle base 222 may not be required. Needle disengagement may also be facilitated by providing a curved pathway between catcher assembly 240 and sheath 216 through which the needles pass when moved relatively proximally.

Figures 9, 10:
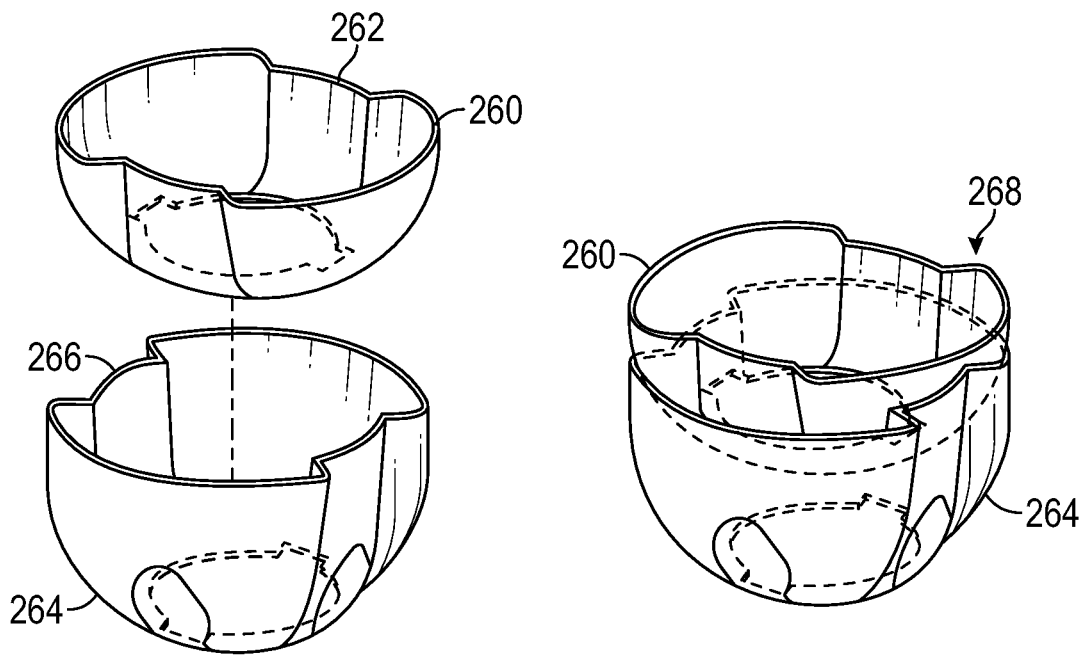
FIGS. 9 and 10 schematically depict a catcher assembly having dished catching elements, according to one embodiment.
Figure 11:
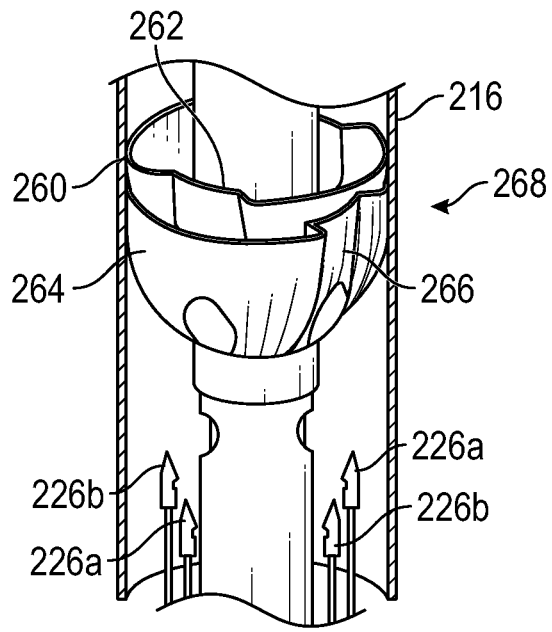
FIGS. 11 and 12 schematically depicts engagement of needle tips with the catcher assembly of FIGS. 9 and 10.
Figure 12:
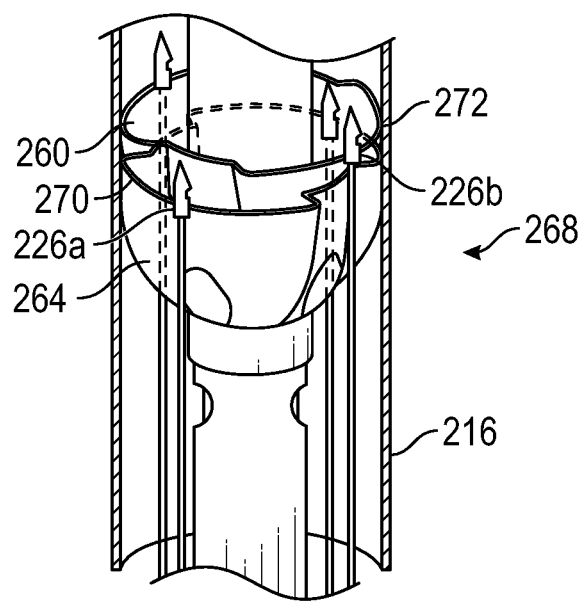

Turning now to FIGS. 9-12, aspects of another embodiment employing nested, dished catching elements 260 and 264 are shown. In FIG. 9, proximal dished catching element 260 is shown with opposing channels 262 that provide similar functionality to the gaps 245 and 247 discussed above. Correspondingly, distal dished catching element 264 also features opposing channels 266, and may be oriented with respect to proximal dished catching element 260 so that each channel 262 and 266 are rotated approximately 90° with respect to each other for a four needle embodiment. As schematically shown in FIG. 10, dished catching elements 260 and 264 may be nested together to form catcher assembly 268, which is shown coaxially disposed within sheath 216 in FIG. 11. At this stage, needle tips 226 have been driven proximally so that they extend within sheath 216, but are still distal of catcher assembly 268. Upon further proximal movement as shown in FIG. 12, all the needle tips 226 have been advanced to a proximal position past catcher assembly 268. Accordingly, when the needles are returned distally, a first subset of needle tips 226b will be engaged by proximal dished catching element 260 at first capture point 272, while a second subset of needle tips 226a are aligned with channel 262 and will not be engaged by proximal dished catching element 260. Likewise, the first subset of needle tips 226b will not be engaged by distal dished catching element 264 because they are aligned with channel 266, but the second subset of needle tips 226a will be engaged by distal dished catching element 264 after distal movement to second capture point 270. Thus, at a first time, needle tips 226b are engaged by proximal dished catching element 260 at first capture point 272 and needle tips 226a are engaged at a subsequent second time by distal dished catching element 264 at second capture point 270, and this asynchronous capture represents a reduced actuation force as described above.

Figure 13:
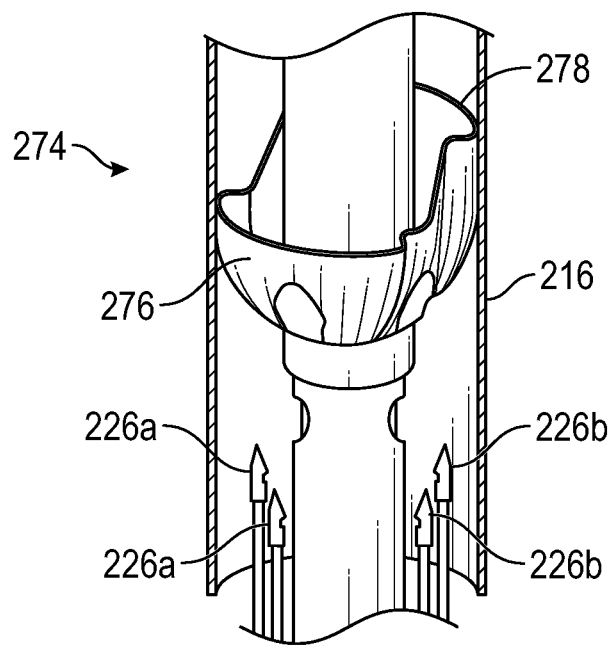
FIG. 13 schematically depicts a catcher assembly having a single catching element, according to one embodiment.

Yet another embodiment is schematically shown in FIG. 13, with catcher assembly 274 that features a single chair-shaped catching element sized to fit within sheath 216 and create a first capture point 278 that is relatively more proximal than a second capture point 276. In this configuration, the capture points engage adjacent rather than opposing needle tips. For example, it may be seen that needle tips 226b will be engaged and captured by first capture point 278 as the needles are returned distally after having been advanced proximally beyond catcher assembly 274. Correspondingly, needle tips 226a will then be captured after further distal motion of the needles at second capture point 276. Once more, this asynchronous capture results in a reduction in the necessary actuation force as compared to designs in which the needles are captured simultaneously.

Figure 14:
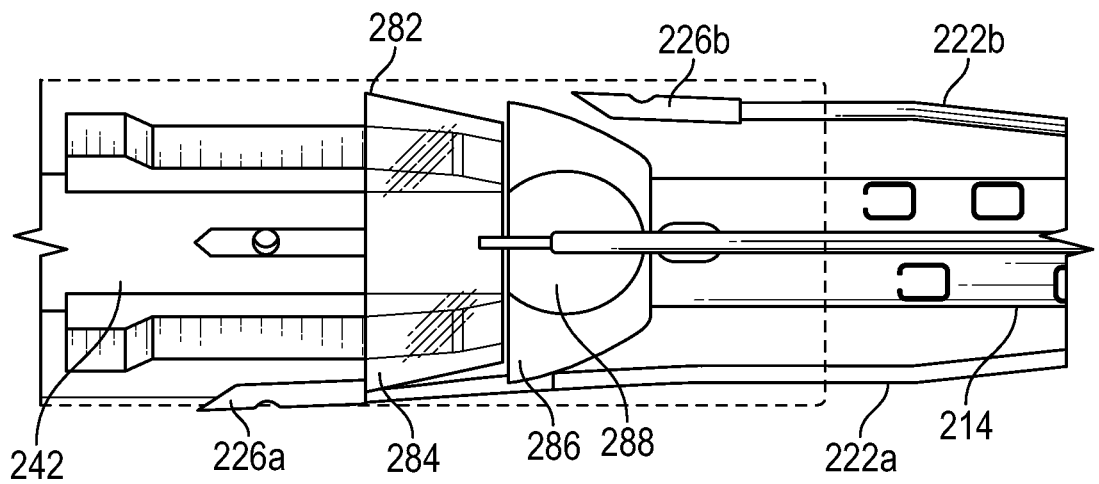
FIG. 14 schematically depicts a needle deployment assembly featuring different length needles, according to one embodiment.

From the above, it will be appreciated that multiple configurations of a catcher assembly are within the scope of this disclosure and may feature two or more capture points, each of which is configured to engage only a subset of the needles, such as by capturing the needle tips. Likewise, different numbers of needles may also be accommodated by appropriate configuration of the one or more catching elements. By employing catcher assemblies with longitudinally displaced capture points, needles that are first driven proximally through the tissue to be sutured to a position that is proximal of the catcher assembly and then returned distally while being maintained in the same longitudinal position relative to each other will be captured at different times as described. However, other mechanism for asynchronously capturing the needles are also within the scope of this disclosure. For example, FIG. 14 schematically depicts catcher assembly 280 with a single circumferential capture point 282 created by the edge of catcher dish 284 positioned proximally of a stabilizer interface 286. Both catcher dish 284 and stabilizer interface 286 may be carried by catcher tube 242. In this embodiment, the asynchronous capture may involve employing needle bases having different relative lengths. For example, one or more needle bases 222a may be relatively longer than one or more needle bases 222b (only one of each is shown in this view for the sake of clarity, but any suitable number may be employed). As a result, after all the needle tips 226 have been advanced proximally past catcher assembly 280 and needle deployment assembly 212 (not shown in FIG. 14) is returned distally, needle tips 226b with the relatively shorter needle bases 222b will engage catcher dish 284 at a first time and needle tips 226a with the relatively longer needle bases 222a will engage catcher dish 284 at a second time subsequent to the first time. As in the above embodiments, the asynchronous capture of the needles represents a reduction in the actuation force as compared to what would be required to capture all the needles simultaneously. In this embodiment, one subset of the needles may have a first length and another subset may have a second, different length, however other modifications are possible by employing three or more different lengths or even by having each needle exhibit a different length.

The material of stabilizer interface 286 may be selected to form a rigid connection with stabilizer 214 while the material of catcher dish 284 may be selected to exhibit the resilience or friction properties described above to allow needle tip 226 to pass in the proximal direction but resist withdrawal in the distal direction. In one aspect, catcher dish 284 may be formed from titanium alloys, such as Ti6Al4V, stainless steel, or other similar materials. In one aspect, catcher dish 284 may be configured to allow needle tips 226 to penetrate the material such that sufficient engagement is created to retain needle tips 226 when needle bases 222 are withdrawn. Similarly, catcher dish 284 may have slits through which needle tips 226 pass when moved to the proximal position. The proximal deflection of the material around the slits when needle tips 226 pass from the proximal side to the distal side may create an interface to facilitate retention of needle tips 226. Stabilizer interface 286 may include guides 288 or similar structural features to help guide needle tips 226 as they travel in the proximal direction. In one aspect, catcher dish 284 may exert a light, outward force on sheath 216. The conical shape of catcher dish 284 may act to guide needle tip 226 through the space between sheath 216 and catcher assembly 280. Where catcher dish 284 contacts sheath 216, the material may slightly deform inward to allow needle tip 226 penetration. When needle tip 226 has completely passed the edge of catcher dish 254 adjacent the inner surface of sheath 216, the material may rebound towards sheath 216 to function as mechanical stop against movement in the distal direction. Accordingly, when needle deployment assembly 212 is retracted, needle tip 226 may be detached from needle base 222. Any gap between catcher dish 284 and sheath 216 will substantially close once needle base 222 is retracted. Needle tip 226 carrying suture material 250 (not shown here for clarity) may then be retained proximal to catcher dish 284.

Described herein are certain exemplary embodiments. However, one skilled in the art that pertains to the present embodiments will understand that the principles of this disclosure can be extended easily with appropriate modifications to other applications.

What is claimed is:

1. A suture delivery device for suturing an opening on tissue comprising:
   an elongated deployment shaft;
   a needle deployment assembly carried by the shaft, including a plurality of needles carrying suture material configured to have an insertion profile at a distal position and to deflect radially outwards to a piercing angle when moved proximally relative to the shaft;
   a stabilizer carried by the shaft at a location proximal of the needle deployment assembly, wherein the stabilizer is reconfigurable between an unexpanded insertion profile and an expanded profile;
   a catcher tube coaxially and slidably disposed over the shaft having a catcher assembly at a distal end, wherein the catcher assembly and needle deployment assembly are configured to asynchronously engage and retain at least a portion of each of the plurality of needles carrying the suture material when the needles are passed through the tissue to be sutured to a proximal position beyond the catcher assembly and then returned distally such that distal movement of the needle deployment assembly causes a first subset of the plurality of needles to engage the catcher assembly at a first time and continued distal movement of the needle deployment assembly causes a second subset of the plurality of needles to engage the catcher assembly at a second time subsequent to the first time; and a sheath coaxially and slidably disposed over the catcher tube, wherein a distal end of the sheath is configured to sandwich tissue to be sutured against the stabilizer when expanded.

2. The suture delivery device of claim 1, wherein an actuation force associated with engaging the first subset of the needles and an actuation force associated with engaging the second subset of the needles is each less than an actuation force required to engage all the needles simultaneously.

3. The suture delivery device of claim 1, wherein the catcher assembly is configured to engage a detachable needle tip of each of the plurality of needles.

4. The suture delivery device of claim 1, wherein the catcher assembly comprises a plurality of capture points.

5. The suture delivery device of claim 4, wherein the plurality of capture points are longitudinally spaced with respect to each other.

6. The suture delivery device of claim 4, wherein each of the plurality of capture points is created by a catching element.

7. The suture delivery device of claim 6, wherein each catching element is configured to only engage a different subset of the needles.

8. The suture delivery device of claim 6, wherein each catching element has a disk configuration.

9. The suture delivery device of claim 6, wherein each catching element has a dished configuration.

10. The suture delivery device of claim 9, wherein the catcher assembly comprises nested dished catching elements.

11. The suture delivery device of claim 4, wherein a single catching element defines the plurality of capture points.

12. The suture delivery device of claim 11, wherein the catching element has a chair shaped configuration.

13. The suture delivery device of claim 1, wherein the catcher assembly has a single capture point and the plurality of needles comprises a first subset of needles having a first length and a second subset of needles having a second length, such that the second length is shorter than the first length.

14. A method for delivering a suture comprising:
providing an elongated deployment shaft, a needle deployment assembly carried by the shaft, including a plurality of needles carrying suture material, a stabilizer carried by the shaft at a location proximal of the needle deployment assembly, a catcher tube coaxially and slidably disposed over the shaft having a catcher assembly at a distal end, and a sheath coaxially and slidably disposed over the catcher tube;
advancing the elongated deployment shaft to a desired position in a body;
reconfiguring the stabilizer from an unexpanded insertion profile to an expanded profile;
sandwiching tissue to be sutured between a distal end of the sheath and the expanded stabilizer;
deflecting the plurality of needles radially outwards to a piercing angle from an insertion profile at a distal position with proximal movement relative to the shaft;
moving the plurality of needles to a proximal position beyond the catcher assembly by passing through the tissue to be sutured;
engaging the catcher assembly with a first subset of the plurality of needles at a first time when moved distally from the proximal position,
engaging the catcher assembly with a second subset of the plurality of needles at a second time subsequent to the first time after further distal movement;
retaining at least a portion of each of the plurality of needles carrying the suture material with the catcher assembly; and
returning a portion of each of the plurality of needles not retained by the needles to the insertion profile at the distal position.

15. The method of claim 14, wherein an actuation force associated with engaging the first subset of the needles and an actuation force associated with engaging the second subset of the needles is each less than an actuation force required to engage all the needles simultaneously.

16. The method of claim 14, wherein the catcher assembly comprises a plurality of capture points and wherein the first subset of needles only engages a first capture point and the second subset only engages a second capture point.

17. The method of claim 14, wherein the plurality of needles comprises a first subset of needles having a first length and a second subset of needles having a second length, such that the second length is shorter than the first length, and wherein the catcher assembly engages the first subset of needles at the first time and engages the second subset of needles at the second time.

18. The method of claim 14, wherein engaging the catcher assembly with the plurality of needles allows a detachable needle tip of each needle to be retained.

* * * * *